United States Patent [19]
McKittrick

[11] Patent Number: 5,123,278
[45] Date of Patent: Jun. 23, 1992

[54] PRESSURE TESTER AND METHOD

[75] Inventor: Merle McKittrick, Denver, Colo.

[73] Assignee: Ball Corporation, Muncie, Ind.

[21] Appl. No.: 656,738

[22] Filed: Feb. 19, 1991

[51] Int. Cl.$^5$ .................................................. G01M 3/32
[52] U.S. Cl. .......................................... 73/52; 73/49.3
[58] Field of Search ................... 73/52, 49.3, 45.4, 37; 209/591; 222/5

[56] References Cited

U.S. PATENT DOCUMENTS

| | | | |
|---|---|---|---|
| 2,749,743 | 6/1956 | Foster | 73/49.3 |
| 2,999,264 | 9/1961 | Stearns | 222/5 X |
| 3,907,490 | 9/1975 | Schaller | 222/5 X |
| 3,958,448 | 5/1976 | Willis et al. | 73/37 |
| 4,555,935 | 12/1985 | Elert | 73/52 |

*Primary Examiner*—Hezron E. Williams
*Assistant Examiner*—Joseph W. Roskos
*Attorney, Agent, or Firm*—Gilbert E. Alberding

[57] ABSTRACT

A pressure tester (50) is provided for safely and efficiently buckle testing a container (120). A housing (52) encloses a test chamber (54) and the related operating equipment. The chamber (54) includes a neck block (80) and a cradling assembly (82) for holding the container (120) therein. Upon activation of a test cycle, the container (120) is punctured on a domed end (124) by a hollow needle (100) which fits within a domed pedestal (94). The container (120) is pushed into the neck block (80) where an outwardly sloping surface (130) generally matches a neck (126) of the container (120). A flexible seal (134) is fitted within a groove (132) in the surface (130) which provides flex without support if the container (120) expands during the test.

33 Claims, 6 Drawing Sheets

PRESSURE TESTER AND METHOD

FIELD OF THE INVENTION

This invention relates in general to testing devices, and in particular to an improved testing device for pressure testing containers.

BACKGROUND OF THE INVENTION

Seamless cans such as are formed by a drawing and ironing process are widely used for soft drink containers, beer containers, etc. While can manufacturers prefer to form the cans with as little material as necessary to save on costs, certain requirements must be met for the safety of consumers. The cans must be able to withstand both external and internal pressures that may be encountered during storage and use. For example, cans used for soft drinks and beer must be able to withstand external pressure from stacking as well as internal pressure from the liquids therein due to temperature and atmospheric pressure changes as well as carbonation.

One important test that cans ends must be able to withstand is a buckle test which is a test of the strength of the components of the can end to resist internal pressures and requires that a can end withstand a pressure change from 0-90 psi in 20 seconds or less without failure. Failures can occur at the neck of the can, along a seam of the can or along the interface between the pull tab and the can top. One known device for testing buckle strength uses an empty but sealed can which is inserted into a holder and then placed within a box. A lid to the box is closed over the can which simultaneously punctures the side of the can with a hollow needle. Air is then pumped through the needle into the can until the can end buckles (or some other failure occurs, such as a seam failure or dome reversal). Due to the design of the holder, some support is provided for the structure of the can by contact therewith. Thus, although not quantified, the tester may not provide an accurate indication of the actual buckle strength of the can end.

Additionally, puncturing the side of the can tends to form a crease or deflection in the side of the can due to the typically long, thin and unsupported sidewalls. Some air must be pumped into the can just to force the can to redeflect and seal around the puncturing device. Creasing the can with the needle also causes a weakening of the can which may tend to distort any results of the test. Additionally, due to the structure of the prior art tester, there is a potential for injury to an operator from projectiles (pieces of the can) escaping the box and from extremely loud explosions when the can fails at a seam.

Another testing apparatus is disclosed in U.S. Pat. No. 3,958,448 to Willis et al., May 25, 1976. The Willis device is primarily designed for pressure testing bottles by puncturing a cap on the top of the bottle. In operation, the bottle is placed on a stand in an up-side-down orientation followed by the puncturing of the cap by a hollow needle. A container retaining member limits upward movement of the bottle by placing a cross-bar over the bottom end thereof. The retaining member is positioned by an adjustable slide arrangement to retard movement of the bottle off the needle. The bottle is first placed in the apparatus and the top is manually punctured by pushing the bottle down onto the needle. The container retaining member is then adjusted to provide a desired gap between the end of the bottle and the cross bar. Thus Willis is primarily a manually operated device that requires repeated readjustment of the container retaining member for various container sizes.

Another testing apparatus is disclosed in U.S. Pat. No. 4,555,935 to Elert, Dec. 3, 1985. The Elert device uses a hollow needle to puncture a side wall of the container. Thus the Elert device is subject to the same disadvantages as the Reynold's tester as previously described above. Specifically, puncturing the side of the container tends to deform and weaken the container at that point. Additionally, a holder is provided which tends to strengthen and support the sides of the can where contacted thereby. Inaccurate results may be obtained from the Elert tester for the same reasons as with the prior art tester previously described above. Thus, there is a need for a method and apparatus for conducting a buckle test on a container which is convenient, easy and safe to operate, and provides consistently accurate results.

SUMMARY OF THE INVENTION

The present invention disclosed herein comprises a method and apparatus for pressure testing a sealed container which substantially eliminates or reduces problems with previous buckle testers. The present invention allows the pressure testing of a sealed container in a consistent, safe and convenient manner.

In accordance with one aspect of the present invention, a chamber receives the container between a neck block and a domed pedestal. A hollow needle is positioned in the domed pedestal for penetration of an end of the container. Once the end of the container is penetrated, fluid is pumped into the container through the needle. A pressure gauge is provided for monitoring of the pressure at which the container fails or buckles.

In another aspect of the present invention, the neck block has a hole therethrough with a diameter at least slightly larger than corresponding diameters of a neck portion of the container. A flexible seal is applied around the internal circumference of the hole for engagement with the neck portion of the container. As pressure is increased within the container, the flexible seal allows expansion of the neck portion without adding strength thereto. Thus a more accurate test of the buckle strength of the can end is achieved than with the known prior art devices.

The domed (convex) pedestal is provided for engagement with a domed (concave) end of the container. The needle is positioned within the center of the domed pedestal and is interconnected to a pressurized fluid source. In operation, the container is placed between the neck block and the domed pedestal. An activation switch is utilized to cause the domed pedestal to engage and the needle to puncture the domed end of the container. Pressurized fluid is then injected into the container until failure occurs based upon its own structure without being strengthened by the tester.

It is a technical advantage of the present invention that more accurate testing of the buckle strength of a container is allowed. The neck block allows some flex of the neck portion of the container without adding strength thereto. It is a further technical advantage of the present invention that the domed pedestal reduces the likelihood of dome reversal which tends to distort test results.

BRIEF DESCRIPTION OF THE DRAWINGS

For a more complete understanding of the present invention and for further advantages thereof, reference is now made to the following Detailed Description taken in conjunction with the accompanying Drawings, in which.

DETAILED DESCRIPTION OF THE INVENTION

Figure 1:
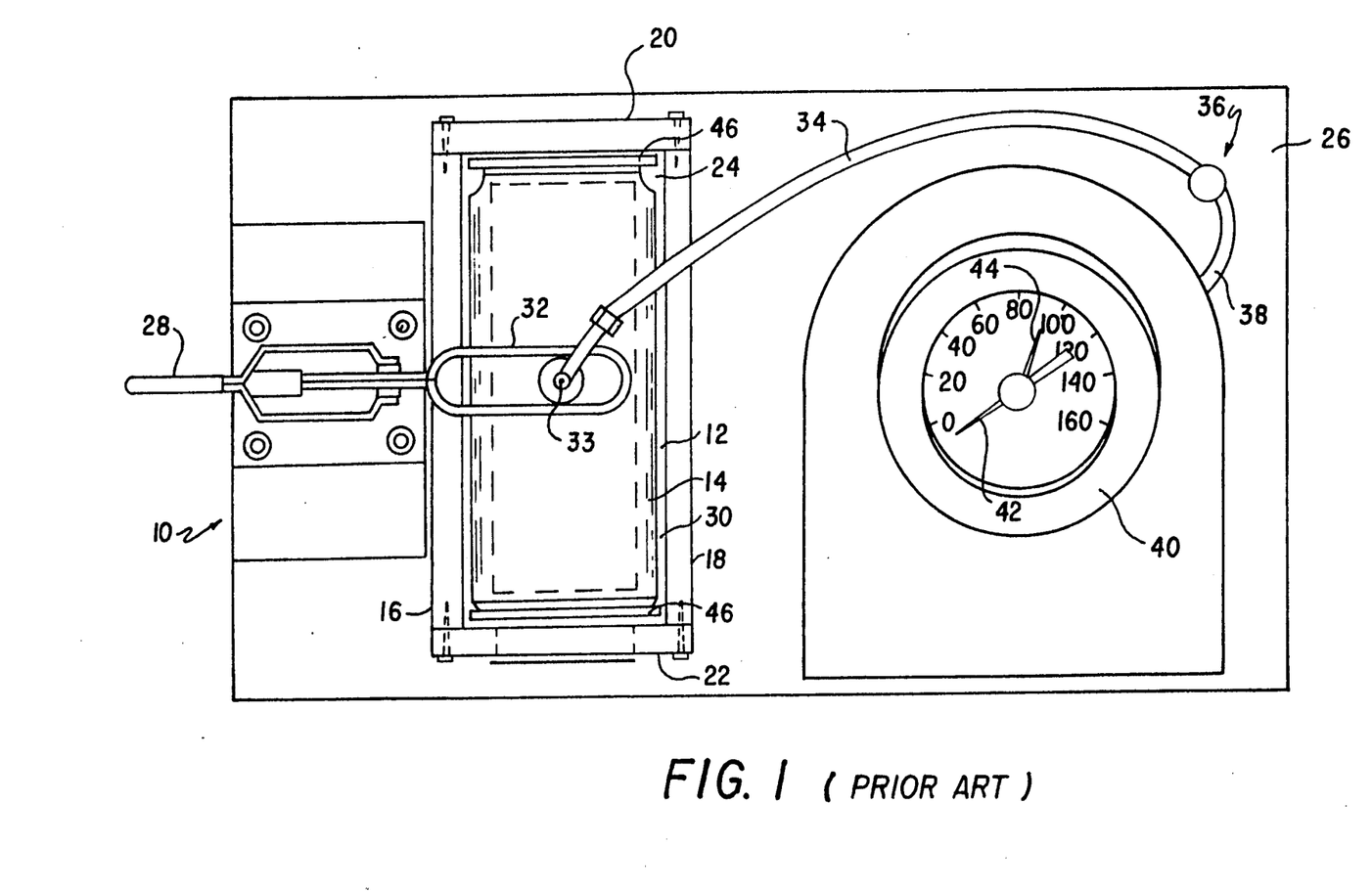
FIG. 1 is a top plan view of a tester constructed in accordance with the prior art.

Referring to FIG. 1, a top plan view of a buckle tester constructed in accordance with one prior art device is generally identified by the reference numeral 10. The buckle tester 10 comprises a test chamber 12 for receiving and testing a can 14. The test chamber 12 generally comprises a rectangular chamber having sidewalls 16 and 18 and end walls 20 and 22. A bottom surface 24 of the test chamber 12 comprises a portion of a support platform 26. Hingedly attached to the chamber 12 by a control lever 28 is a top 30. The sidewalls 16-18, end walls 20-22, and the top 30, comprise plexiglass or other translucent material having sufficient strength to withstand explosion of the can 14. Fixed to the top 30 by a connector portion 32 to the control lever 28 is a puncturing needle 33 and a pressurized fluid line 34.

Pressurized fluid is provided to the line 34 from a source, generally indicated at 36, which comprises a pump or a "factory air" line. Interconnected to the source 36 and the line 34 by a line 38 is a pressure gauge 40. The pressure gauge 40 is provided with a readout dial in pounds per square inch with a needle 42 for indicating pressure and a stop needle 44 for indicating maximum pressure.

In operation, the can 14 is placed within a holder 46 and then inserted into the test chamber 12. The top 30 is closed over the chamber 12 by moving the control lever 28. As the top 30 closes over the chamber 12, the needle 33 at the end of the pressurized fluid line 34, penetrates a sidewall of the can 14. By engaging a switch (not shown) pressurized fluid is pumped from the source 36 through the line 34 into the can 14. As the can 14 is pressurized, the needle 42 registers the pressure. Upon reaching the point of failure, the stop needle 44 will remain at the highest pressure and, therefore, provides a readout of the failure pressure. There is no sound proofing or safety devices on the tester 10 and, therefore, if the can 14 should explode, projectiles may escape from the test chamber 12 and strike an operator. Additionally, any explosions typically result in a loud blast which may startle or injure the operator or others in the vicinity.

Figure 2:
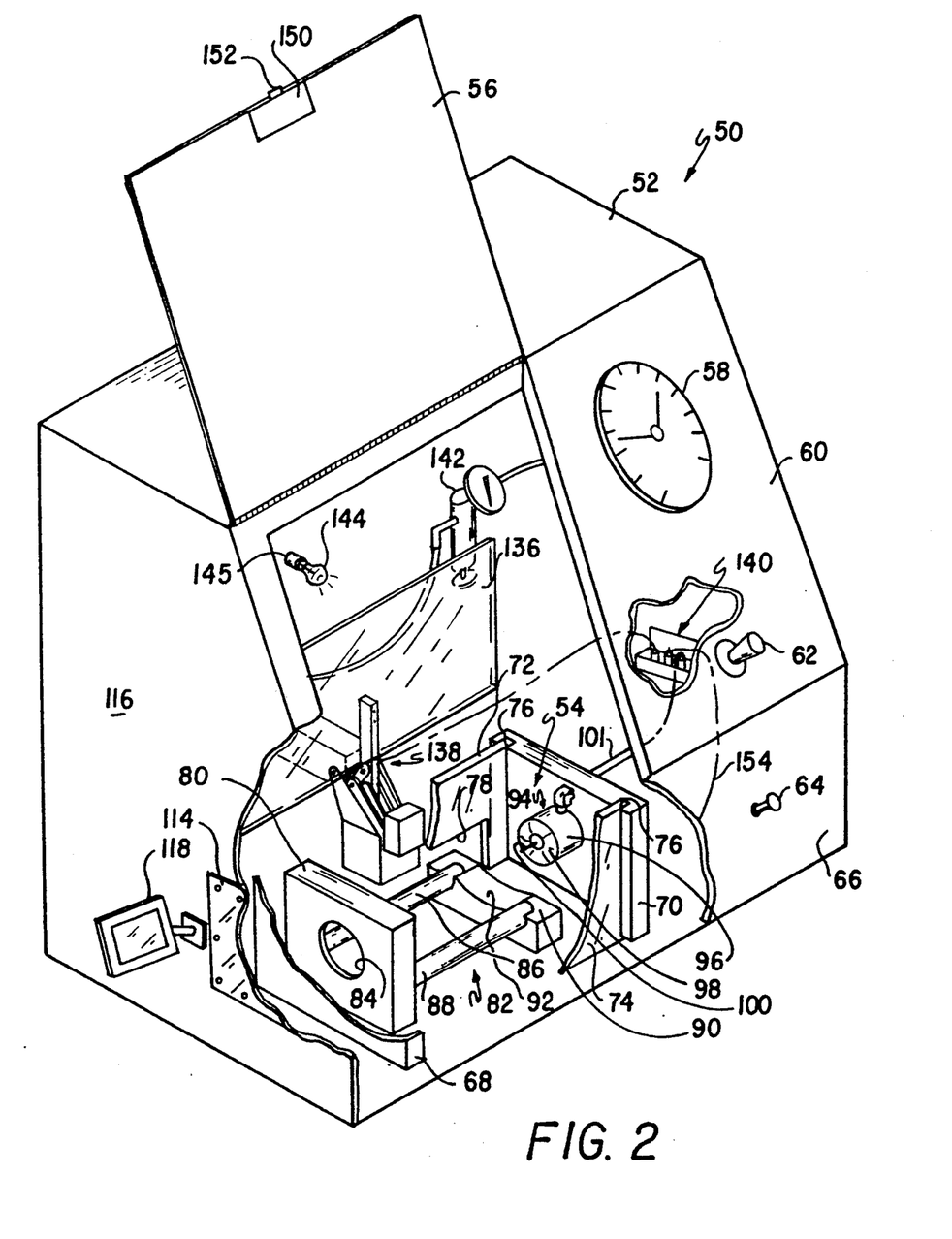
FIG. 2 is a partially cutaway perspective view of a tester constructed in accordance with the present invention.

Referring to FIG. 2, a partially cutaway perspective view of a pressure tester constructed in accordance with the present invention is generally identified by the reference numeral 50. The tester 50 comprises a housing 52 within which is positioned a test chamber 54. The housing 52 is provided with a hinged door 56 which may comprise, for example, plexiglass, to allow visual inspection as well as physical access to the test chamber 54. A pressure gauge 58 is installed in a front panel 60 along with a pressure regulator 62. Although not shown, it is to be understood that a digital readout and printing device could be attached to the tester 50 to provide printed verification of the pressure readout. A control switch 64 passes through a vertical panel 66 into the interior of the housing 52.

The hinged door 56 is provided with a latching mechanism 150. The mechanism 150 has a spring loaded latch 152 which automatically engages a striker plate (not shown) on the housing 52 when the door 56 is closed. Upon engagement of the striker plate by the latch 152, a signal is sent to valves 140 via a line 154 to indicate the door 56 is closed. This signal allows, upon activation of the control switch 64, initiation of a test cycle.

The test chamber 54 is fixed within the housing 52 and comprises a first end wall 68, a second end wall 70, and first and second side walls 72 and 74. The walls 68-74 preferably comprise plexiglass or any other suitable material which is sufficiently transparent to allow visual observation of the testing of a container therein. The first and second end walls 68-70 are provided with slots 76 to allow the side walls 72-74 to be slidably inserted and removed therefrom. By allowing the slidable insertion and removal of the side walls 72-74, if the material thereof become damaged so as to reduce visibility therethrough, the sidewalls 70-72 may simply be replaced. The sidewall 72 is also provided with a cutout 78 to allow the escape of pressurized fluid from the chamber 54 when a container therein fails thus reducing stress on the chamber 54.

The chamber 54 is provided with a hinged cover 136 which may also comprise plexiglass to allow viewing therethrough as well as to provide safety for an operator. A closing mechanism 138 serves to hingedly close and secure the cover 136 over the chamber 54. As will be subsequently described in greater detail, valves 140 are provided to automatically close the cover 136 and initiate a test cycle one the hinged door 56 is closed.

Within the chamber 54 is a neck block 80 and a cradling assembly 82. The neck block 80 comprises a block of metal or other suitable material having a hole 84 therethrough. As will be subsequently described in greater detail, a hole 84 in the neck block 80 has an internal circumference shaped to generally match the shape of a neck of a container placed within the chamber 54 for testing thereof. The cradling assembly 82 comprises first and second connecting rods 86-88 and a cradle 90. Upon placement of a container within the chamber 54, the container will rest upon the connecting rods 86-88 and the cradle 90. The cradle 90 has an arcuate surface 92 for generally matching the outside dimensions of a container.

Opposite the neck block 80 within the chamber 54 is a domed pedestal 94. The domed pedestal 94 comprises a generally cylindrical body 96 having an arcuate (generally convex) top 98. A passageway (not shown) passes through the cylindrical body 96 for interconnecting a hollow needle 100 to a source (not shown) of pressurized fluid through a connector line 101 from the valves 140.

Also positioned within the housing 52 are various control assemblies such as a valve 142 and the valves 140 for the regulation of fluid pressure, as is well-known in the art. Although not shown, it is to be understood that a source of pressurized air is interconnected to the housing 52. Additionally, various interlocks are provided to insure that activation of the test cycle does not occur unless the hinged door 56 is closed, and the cover 136 for the test chamber 54 is in place.

A window 114 which may comprise, for example, plexiglass, is positioned on an end 116 of the housing 52. Positioned proximate the window 114 is a reflective device 118 such as a mirror. The window 114 and reflective device 118 allow an operator to observe the buckle testing of a container within the chamber 54 from various angles while standing in front of the housing 52. The insides of the housing 52 are also covered with an appropriate sound insulating material 144 such as, for example, foam rubber. A light source 145 such as a standard light bulb may be provided within the housing 52 for assisting with observation therein.

Figure 3:
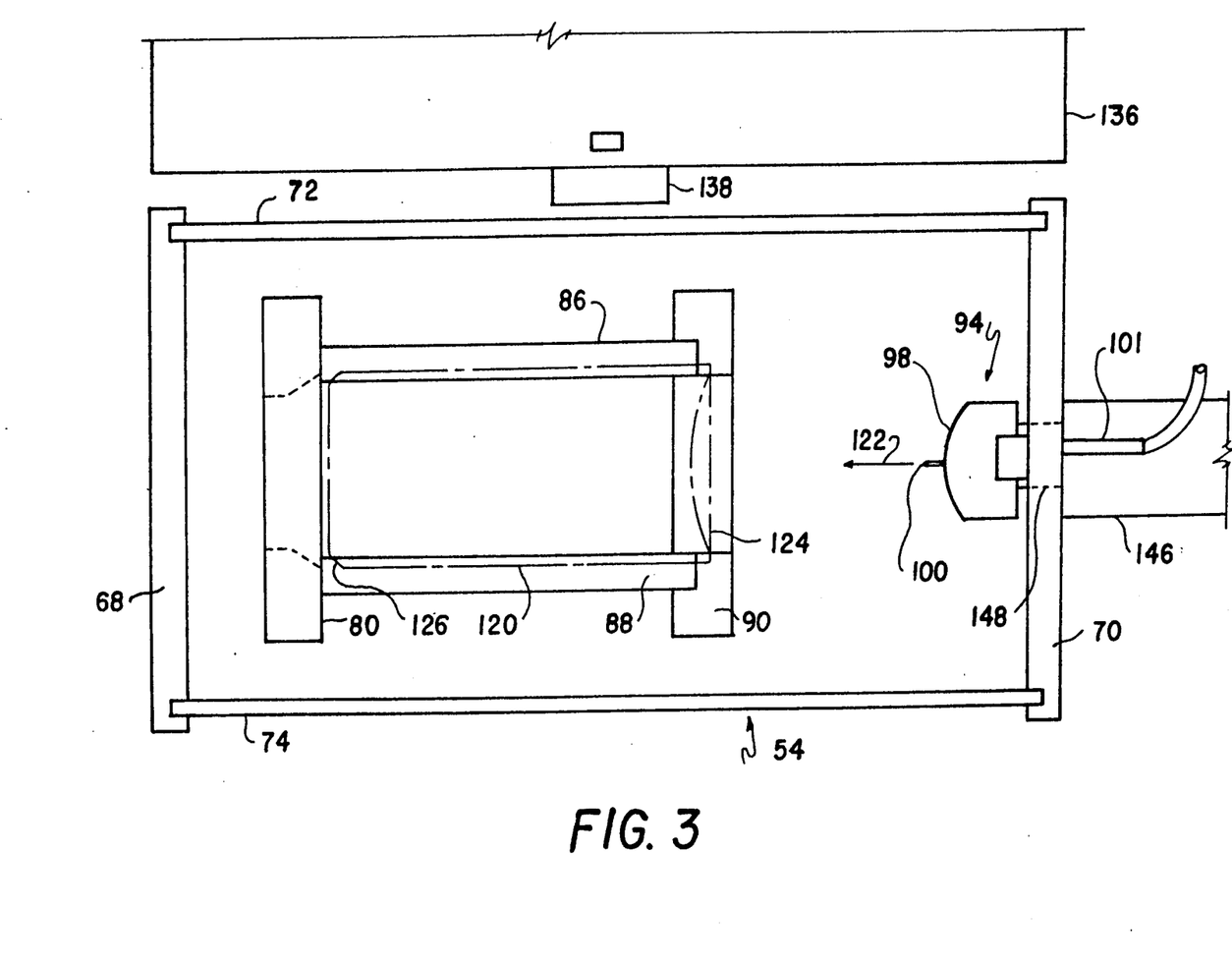
FIG. 3 is a top plan view of the test chamber of the tester of FIG. 2.

Referring to FIG. 3, a top plan view of the test chamber 54 is illustrated. When a container 120 (shown in phantom) is placed on the cradling assembly 82, it is held in position by the connecting rods 86-88 and the cradle 90. Upon activation of the control lever 64, (assuming that the door 56 is closed) the cover 136 is closed and a power cylinder 146 is activated. A power cylinder piston 148 is extended from the power cylinder 146 to move the domed pedestal 94 in a direction indicated by an arrow 122. As the power piston 148 moves the pedestal 94 in the direction 122, the air connector line 101 slides through the second end wall 70 to move along with the pedestal 94. Upon coming into contact with a domed (generally concave) end 124 of the container 120, the hollow needle 100 initially pushes the container 120 further in the direction 122 until a tapered neck 126 of the container 120 is within the neck block 80. Once the container 120 is seated within the neck block 80, further movement of the domed pedestal 94 in the direction 122 causes the hollow needle 100 to penetrate the domed end 124 of the container 120. Due to the arcuate top 98 of the domed pedestal 94, there is a general matching with the domed end 124 of the container 120.

Figure 4:
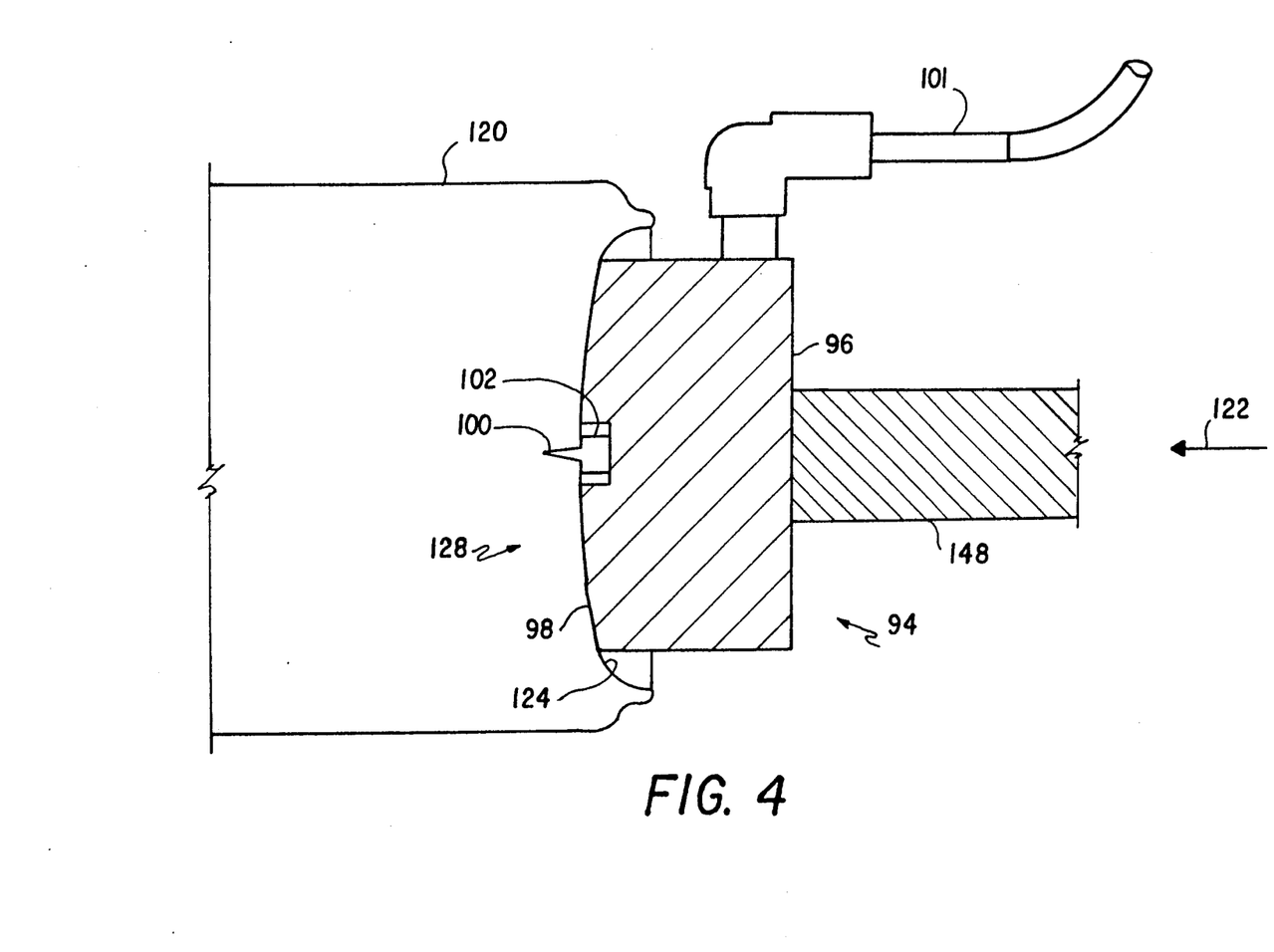
FIG. 4 is a cross-sectional view of the domed pedestal of the present invention.

Referring to FIG. 4, a cross-sectional view of the pedestal 94 with the hollow needle 100 puncturing a container 120 is shown. A seal 102 is provided around the needle 100 to help seal the hole formed in the container 120 by the needle 100. As can be seen in FIG. 4, the arcuate top 98 of the pedestal 94 approximately matches the arcuate surface of the domed end 124 of the container 120. Due to this approximate matching of surfaces, and in conjunction with the neck block 80, the tester 50 reduces the likelihood of dome reversal during buckle testing. Dome reversal is caused by pressure in the container pushing the domed end 124 in a direction as indicated by arrow 128 into a shape generally opposite that shown in FIG. 4. If dome reversal occurs, an inaccurate buckle test result may be obtained, and, therefore, it is preferable to prevent dome reversal. It is to be understood that the tester 50 may be used to test dome reversal strength if desired. By placing the container 120 with the domed end 124 adjacent the neck block 80, pressurization of the container 120 will test dome reversal. It is, however, preferable to use a container having a shell end without a pull tab thereon for dome reversal testing.

Figure 5A:
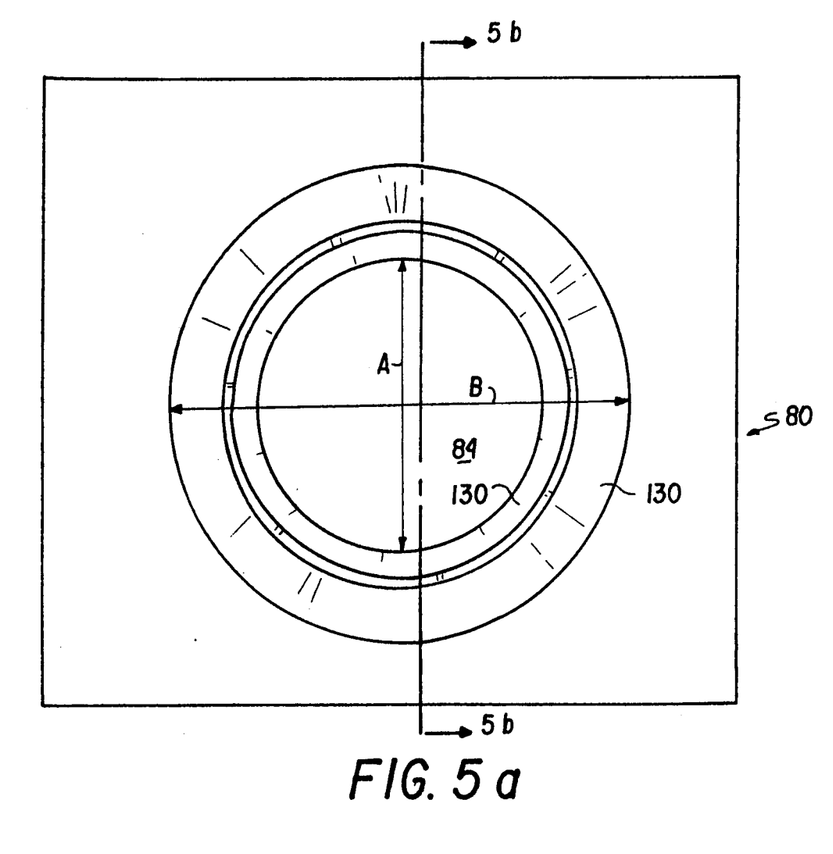
FIGS. 5a and 5b are views of the neck block of the present invention.
Figure 5B:
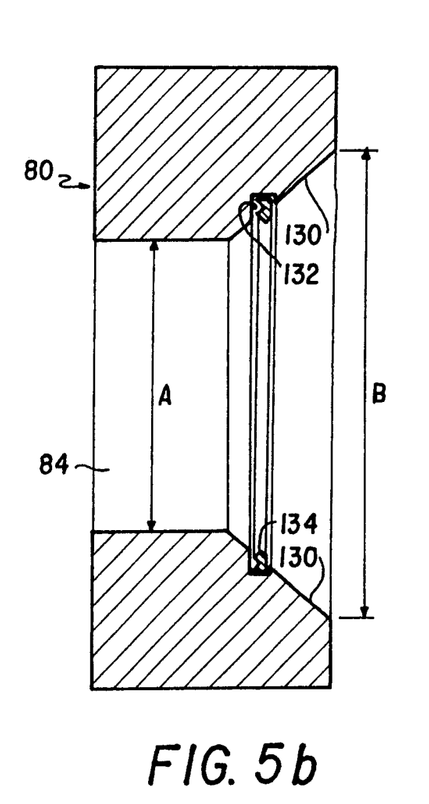

Referring to FIGS. 5a and 5b, end elevation and cross-sectional views of the neck block 80 are shown. As the neck 126 (see FIG. 3) of the container 120 enters the neck block 80 through the hole 84, an outwardly sloping surface 130 is provided to approximately match the shape thereof. Thus the hole 84 has a first diameter A and a second diameter B, wherein the diameter B is greater than the diameter A.

Along the sloping surface 130 is a circumferential groove 132. Within the groove 132 is a flexible seal 134 such as, for example, a Parker seal. The sloping surface 130 is designed to provide a greater diameter along all points thereof than along corresponding portions of an outside diameter of the neck 126 of the container 120 when positioned within the neck block 180. Thus, there is some space between the neck 126 and, the sloping surface 130. The flexible seal 134 serves to contact the neck 126, and along with the sloping surface 130, help align the container 120 within the block 80. During buckle testing of the container 120, the flexible seal 134 allows for expansion of the neck 126 without adding strength to the container 120, and thus a more accurate test can be conducted.

Figure 6:
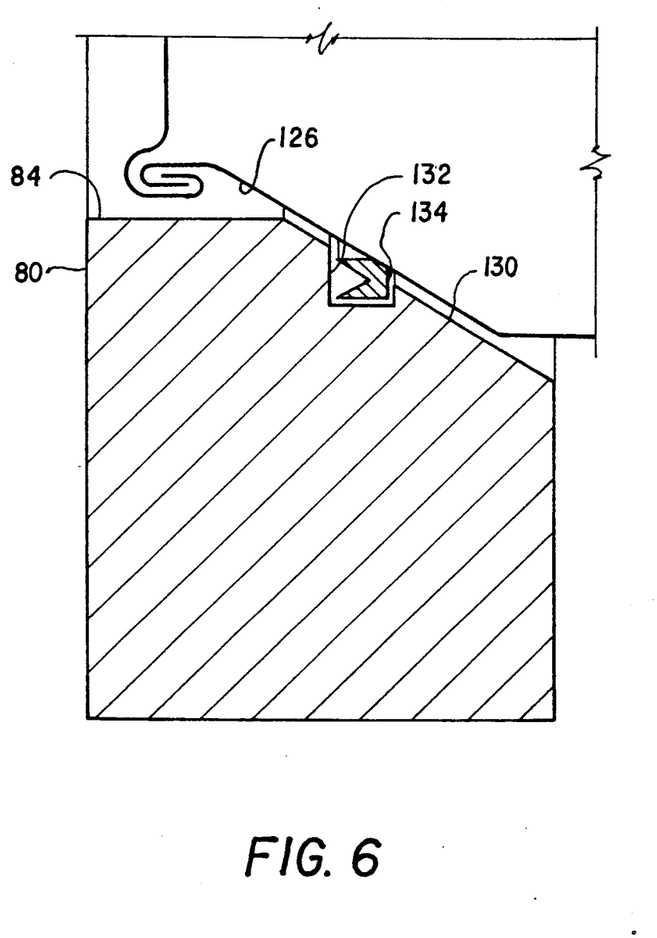
FIG. 6 is a cross-sectional view of a portion of the neck block in contact with the neck of a container.

Referring to FIG. 6, a partial cross-sectional view of the block 80 and the neck 126 is illustrated. As can be seen in FIG. 6, the neck 126 slightly compresses the seal 134 when contact is made therebetween. Once the hollow needle 100 penetrates the container 120, the seal 134 may expand slightly approximately to its original shape. Any expansion of the neck 126 due to internal pressurization will cause the seal 134 to be compressed into the groove 132 thus allowing expansion without adding strength to the container 120.

In operation, an operator (not shown) will open the hinged door 56 and place the container 120 on the cradling assembly 82 in the chamber 54. After closing and latching the door 56, the operator initiates the test cycle by activating the control switch 64 on the vertical panel 66. Upon activation of the control switch 64, the valves 140 cause the hinged cover 136 to close the chamber 54. The valves 140 then cause the power cylinder piston 148 to extend from the power cylinder 146 and move the domed pedestal 94 in the direction 122 toward the container 120 and simultaneously provide fluid to the hollow needle 100. Upon contact between the needle 100 and the domed end 124 of the container 120, the container 120 is also moved in the direction 122. Due to the neck block 80 and the sloping surface 130 therein, the neck 126 of the container 120 is centered within the hole 84. Thus the needle 100 penetrates the domed end 124 of the container 120 in the approximate center thereof once the container is restrained from further movement in the direction 122 by the block 80. As the needle 100 penetrates the container 120, the puncture formed therethrough is sealed by the seal 102 and by the matching of the surfaces of the domed end 124 and the arcuate top 98. Fluid supplied from the line 101 through the needle 100 is pumped into the container 120 and registered on the pressure gauge 58. When the container 120 buckles or fails, the failure pressure is recorded by the gauge 58, as is well known in the art. After failure, the pedestal 94 returns to its starting position distal the container 120 as shown in FIG. 3.

Due to the present invention, an operator is able to conduct pressure tests in a safer environment. Observation of the test is easier due to the use of the reflective device 118. The operator and others in the vicinity are less likely to be startled due to the use of sound insulating material 144. Additionally, more consistent test results are available due to the advantages of the present invention.

Due to the seal 134 and the sloping surface 130, the container 120 is properly aligned with the needle 100. The seal 134 provides room for expansion of the neck 126 of the container 120 without adding strength thereto. Additionally, the arcuate surface 92 of the domed pedestal 94 approximately matches the domed end 124 of the container 120 and thus reduces the likelihood of dome reversal. Also, the easily replaced sidewalls 72 and 74 allow any damage thereto from container explosions to be quickly dealt with. The cut-out 78 in the sidewall 72 reduces damage to the chamber 54 by allowing trapped fluids to harmlessly escape.

Although the present invention has been described with respect to a specific preferred embodiment thereof, various changes and modifications may be suggested to one skilled in the art, and it is intended that the present invention encompass such changes and modifications as fall within the scope of the appended claims.

What is claimed is:

1. A pressure testing apparatus for a container having a tapered neck, a concave domed end, and a separate end piece attached to and closing another end of the container, comprising:
    means for engaging at least a portion of the neck of the container spaced from the end piece, said means for engaging being free from substantial engagement with the end piece;
    a convex domed pedestal for engaging the concave domed end of the container; and
    means for pressurizing the container, wherein the container is held between said means for engaging and said domed pedestal while said means for pressurizing fills the container with a fluid to conduct the test.

2. The apparatus of claim 1, wherein said means for pressurizing comprises:
    a hollow needle interconnected through said domed pedestal to a source of pressurized fluid.

3. The apparatus of claim 1, further comprising:
    means for enclosing the container.

4. The apparatus of claim 3, further comprising:
    a chamber within said means for enclosing, said chamber containing said means for engaging and said domed pedestal.

5. The apparatus of claim 3, wherein said means for enclosing comprises:
    a housing having a hinged door;
    a pressure gauge fixed to an exterior surface of said housing; and
    control means for initiating a test cycle.

6. The apparatus of claim 5, wherein said control means further comprises:
    means for detecting when said door is in a closed position.

7. The apparatus of claim 1, wherein said means for engaging the neck comprises:
    a neck block having a hole therethrough for receiving the tapered neck, said hole having a first diameter and a sloping surface tapering outwardly to a second diameter greater than said first diameter, wherein said sloping surface generally matches the tapered neck.

8. The apparatus of claim 7, wherein said sloping surface further comprises:
    a circumferential groove; and
    a flexible seal within said groove for contact with the tapered neck of the container.

9. The apparatus of claim 1, further comprising:
    means for sound-proofing the apparatus.

10. The apparatus of claim 1, wherein said means for engaging comprises:
    compressible sealing means.

11. A pressure testing apparatus for a container having a tapered neck and a concave domed end, comprising:
    means for engaging the domed end of the container;
    a neck block for engaging the neck of the container, said block having a hole therethrough for receiving the tapered neck, said hole having a first diameter and a sloping surface tapering outwardly to a second diameter greater than said first diameter, wherein said sloping surface generally matches the tapered neck; and
    means for pressurizing the container, wherein the container is held between said means for engaging the domed end and said neck block while said means for pressurizing fills the container with a fluid to conduct the test.

12. The apparatus of claim 11, wherein said means for pressurizing comprises:
    a hollow needle interconnected through said domed pedestal to a source of pressurized fluid.

13. The apparatus of claim 11, further comprising:
    means for enclosing the container.

14. The apparatus of claim 13, further comprising:
    a chamber within said means for enclosing, said chamber containing said means for engaging said domed end and said neck block.

15. The apparatus of claim 13, wherein said means for enclosing comprises:
    a housing having a hinged door;
    a pressure gauge fixed to an exterior surface of said housing; and
    control means for initiating a test cycle.

16. The apparatus of claim 15, wherein said control means further comprises:
    means for detecting when said door is in a closed position.

17. The apparatus of claim 11, wherein said sloping surface further comprises:
    a circumferential groove; and
    a flexible seal within said groove for contact with the tapered neck of the container.

18. The apparatus of claim 11, further comprising:
    means for sound-proofing the apparatus.

19. An apparatus for pressure testing a sealed container having a tapered neck and a domed end, comprising:
    a housing;
    an assembly in said housing comprising a chamber for receiving the container, a neck block for engaging the neck of the container and a domed pedestal for engaging a domed end of the container;
    a hollow needle positioned in said domed pedestal for penetrating an end of the container;
    a pressurized fluid source in communication with said hollow needle to allow fluid to enter the container through said needle; and
    control means for initiating flow of said fluid from said source to the container, wherein the container is inserted into said chamber and said control means is activated to test the container.

20. The apparatus of claim 19, wherein said neck block comprises:
    a block having a hole therethrough with an outwardly tapering diameter at least slightly larger than corresponding diameters of the tapered neck of the container when positioned in said block; and flexible sealing means fixed within said hole for engaging the tapered neck.

21. The apparatus of claim 19, wherein said domed pedestal comprises:

a generally cylindrical body having a passageway therein for receiving said hollow needle; and an arcuate end portion connected to said cylindrical body and having a second passageway therethrough for receiving said needle, said arcuate portion being shaped to generally match the domed end of the container to reduce the likelihood of dome reversal.

22. The apparatus of claim 19, further comprising: sound proofing material applied to said housing.

23. The apparatus of claim 19, further comprising:

a door on said housing for allowing access to said chamber.

24. The apparatus of claim 23, wherein said door further includes a spring loaded latch.

25. The apparatus of claim 19, further comprising:

a window through a sidewall of said housing for viewing said chamber; and reflective means attached to said sidewall proximate said window for assisting in viewing of said chamber.

26. The apparatus of claim 19, further comprising:

a light source within said housing for illuminating said housing.

27. The apparatus of claim 19, wherein said chamber comprises:

first and second sidewalls;

first and second end walls having slots therein for slidably receiving said sidewalls; and a cover for enclosing the container within said chamber.

28. The apparatus of claim 27, wherein said walls and said cover comprise plexiglass.

29. The apparatus of claim 27, wherein at least one of said walls has a cut-out therein to allow pressurized fluid to escape from said chamber.

30. The apparatus of claim 19, further comprising:

means for detecting a ready-to-test condition.

31. A method for securing a container to be pressure tested substantially without adding strength to the container, comprising the steps of:

engaging at least a portion of a tapered neck of the container, spaced from a separate end piece attached to and closing an end of the container, with a flexible seal which is positioned in a similarly tapered neck block; and engaging a domed end of the container with a similarly domed pedestal.

32. A method for pressure testing a container, comprising the steps of:

engaging at least a portion of a tapered neck of the container, spaced from a separate end piece attached to and closing an end of the container, with a flexible seal which is positioned in a similarly tapered neck block;

engaging a domed end of the container with a similarly domed pedestal;

piercing said domed end with a needle; and pressurizing the container with fluid passing through said needle into the container until failure occurs.

33. A pressure testing apparatus for a container having a first end, sidewall, and a separate end piece attached to a second end of the container opposite the first end, comprising:

first means for exerting an axial force on the first end of the container;

second means for resisting at least a portion of said axial force, said second means engaging a portion of the sidewall spaced from the second end and compressing due to the exertion of said axial force by said first means; and third means for introducing fluid into the container to pressurize the container.

* * * * *